(12) United States Patent
Noecker et al.

(10) Patent No.: US 7,625,412 B2
(45) Date of Patent: Dec. 1, 2009

(54) COMPOSITION FOR COLORING KERATIN FIBRES

(75) Inventors: Bernd Noecker, Ober-Ramstadt (DE); Frank Golinski, Ober-Ramstadt (DE); Frank Hermes, Seeheim (DE); Ina Braeutigam, Darmstadt (DE)

(73) Assignee: KPSS-Kao Professional Salon Services GmbH, Darmstadt (DE)

( * ) Notice: Subject to any disclaimer, the term of this patent is extended or adjusted under 35 U.S.C. 154(b) by 89 days.

(21) Appl. No.: 11/422,360

(22) Filed: Jun. 6, 2006

(65) Prior Publication Data

US 2006/0272106 A1    Dec. 7, 2006

(30) Foreign Application Priority Data

Jun. 7, 2005    (EP)    ................... 05012200

(51) Int. Cl.
*A61Q 5/10*    (2006.01)
(52) U.S. Cl. ................ 8/405; 8/406; 8/407; 8/409; 8/426; 8/455; 8/516; 8/552; 8/554; 8/561; 8/607; 8/632
(58) Field of Classification Search ............... 8/405, 8/406, 407, 409, 426, 455, 516, 552, 554, 8/561, 607, 632
See application file for complete search history.

(56) References Cited

U.S. PATENT DOCUMENTS

| 4,268,500 A | 5/1981 | Cloninger |
| 5,618,525 A * | 4/1997 | Bunning ................ 424/70.122 |
| 6,616,707 B2 * | 9/2003 | Lorenz ................... 8/405 |
| 2005/0055782 A1 * | 3/2005 | Rollat-Corvol et al. ........ 8/405 |

FOREIGN PATENT DOCUMENTS

| WO | 03/070208 A1 | 8/2003 |
| WO | WO 03/070208 A1 * | 8/2003 |

OTHER PUBLICATIONS

Quest International; "Yogurtene"; Cosmetic Ingredients; Jun. 2000; pp. 1-17.

* cited by examiner

*Primary Examiner*—Eisa B Elhilo
(74) *Attorney, Agent, or Firm*—Norris McLaughlin & Marcus, P.A.

(57) ABSTRACT

Present invention is related to oxidative hair coloring composition comprising yogurt powder for improving combability of hair.

14 Claims, No Drawings

COMPOSITION FOR COLORING KERATIN FIBRES

The present invention concerns a composition for the dyeing keratin fibers especially human hair on the basis of an oxidation dyestuff precursor system reacting with peroxide and comprising yogurt powder for improving combability of hair after oxidative coloration without need of using of further detangling composition.

Combability of hair coloration and especially after oxidative coloration has been observed to be reduced by the use of oxidizing composition which damages the hair. In everyday practice, additional detangling composition known as hair treatments have been usually applied in order to make hair combable. This causes problems first of all time wise and not economical because of the need of additional hair conditioning preparations. The second problem is elution of the dyestuffs especially from hair surface leads to less brilliant colors or, in order to overcome this, high dyestuff comprising compositions must be used.

Several attempts have been made in order to overcome such problems without use of additional hair detangling products. One of them is using cationic compounds in hair colouring compositions which are known to be detangling hair from hair conditioning area. These compounds are cationic polymers and cationic amphiphilic compounds. Incorporation of these leads to some formulation problems as these because of their cationic character interact with other compounds of anionic character which cannot be excluded from formulations.

The present invention starts from the above mentioned problems and aims at proving a hair colouring composition especially oxidative hair colouring composition which at the same time improves hair combability and therefore no need of using additional combability improving preparations.

The inventors have surprisingly found out that use of yogurt powder improves the hair combability unexpectedly when added into the dyeing composition based on oxidative dyes precursors.

In a U.S. Pat. No. 4,268,500, use of yogurt as a natural product for treating scalp and hair is disclosed. Natural yogurt is used simply by rubbing onto hair and scalp according to the method disclosed therein. The document does not disclose any use of yogurt or its extracts and its powders in any modern cosmetic formulation.

In recently published PCT application, WO 03/070208, use of yogurt is disclosed for improvement of non-oxidative hair colouring. The disclosure contains as well shampoo and conditioner compositions to be used for improving colour retention on non-oxidatively coloured hair. The document, however does not deal with oxidative colouring compositions.

Thus, the object of the invention is an oxidative hair coloring composition based on oxidative dyestuffs precursors reacting with peroxide comprising yogurt powder.

Further object of the present invention is the use of yogurt powder for improving hair combability in a oxidative hair colouring composition based on oxidative dyestuffs precursors reacting with peroxide.

Yogurt powder is a raw material prepared by spray drying of natural yoghurt after completion of fermentation. Yogurt powder comprises the following major components:
- approximately 53.5% lactose,
- approximately 25% proteins,
- approximately 7.5% lactic acid,
- approximately 5% minerals and trace elements,
- approximately 1% vitamines, and
- approximately 2% lipids.

Composition of the present invention comprises yogurt powder at a concentration of 0.01 to 5%, preferably 0.05 to 3%, more preferably 0.05 to 2% and most preferably 0.1 to 1% by weight calculated to total composition.

Suitable oxidative dyestuffs precursors are tetraaminopyrimidines, in particular 2,4,5,6-tetraaminopyrimidine and the lower alkyl derivatives thereof; suitable triaminohydroxypyrimidines are, for example 4-hydroxy-2,5,6-triaminopyrimidine, 2-hydroxy-4,5,6-triaminopyrimidine and 5-hydroxy-2,4,6-triaminopyrimidine; suitable mono and diamino dihydroxypyrimidines are, for example, 2,6-dihydroxy-4,5-diaminopyrimidine, 2,4-diamino-6-hydroxy-pyrimidine or 4,6-dihydroxy-2,5-diaminopyrimidine or the water-soluble salts thereof, aminophenol derivatives such as 4-aminophenol, 4-amino-3-methylphenol, 2-chloro-4-aminophenol, 2,6-dichloro-4-aminophenol, 2,4-diamino-phenol, 2,6-dibromo-4-aminophenol and/or 2-aminophenol and water-soluble salts thereof, furthermore, phenylenedimanine derivatives such as 2,5-diamino-toluene, 2-n-propyl or 2-ethyl-p-phenylene-diamine, 2,6-dimethyl-p-phenylenediamine, 2-(2,5-diaminophenyl)ethanol, 1-amino-4-bis-(2'-hydroxy-ethyl) aminobenzene, 2-(2-hydroxyethyl amino)-5-aminotoluene, 4,4'-diaminodiphenylamine, 4-aminodiphenylamine, 2-amino-5-N,N-diethyl aminotoluene, 4-amino-N-ethyl-N-isopropyl aniline, 2-chloro-p-phenylenediamine, 1-β-hydroxyethyl-2,5-diamino-4-chlorobenzene, 1-β-hydroxyethyl-2,5-diamino-4-methyl benzene, 2-methoxy-p-phenylenediamine, N,N-diethyl-p-phenylenediamine, 1-amino-4-β-methoxyethyl aminobenzene, 1-dimethyl-amino-4-aminobenzene, 1-hydroxy-2,5-diamino-4-methyl benzene, 1-hydroxymethyl-2,5-diaminobenzene, 1,3-dimethyl-2,5-diaminobenzene, 1,4-diamino isopropyl benzene and/or 1-amino-4-β-hydroxypropyl aminobenzene or the water-soluble salts thereof, pyrazole derivatives such as 1-hydroxyethyl-4,5-diaminopyrazole, 3,4-diamino-5-hydroxypyrazole, 3,5-diaminopyrazole, 3,5-diamino pyrazol-1-carboxamide, 3-amino-5-hydroxypyrazole, 1-phenyl-2-methylpyrazole, 1-phenyl-3-methylpyrazole-5-one, 3,5-dimethylpyrazole, 3,5-dimethylpyrazole-1-methanol, 1-methyl-4,5-diaminopyrazole, 1-methylethyl-4,5-diaminopyrazole, 1-phenylmethyl-4,5-diaminopyrazole, 1-methyl-4,5-diaminopyrazole, 1-(4-methylphenyl)methyl-4,5-diaminopyrazole, 1-methyl-3-phenyl-4,5-diaminopyrazole and the water-soluble salts.

The total concentration of the oxidation dyestuff precursors and/or their water soluble salts customarily ranges between about 0.05% and 5%, preferably 0.1% and 4%, in particular 0.1% to 3% by weight, calculated to the total hair dyeing composition (excluding the oxidation agent), whereby these figures are always related to the proportion of free base.

The composition according to the invention preferably comprises at least one coupling substance, which can be selected from resorcinol, 2-methyl resorcinol, 4-chlororesorcinol, 2-amino-4-chlorophenol, 5-amino-4-methoxy-2-methylphenol, 3-amino-phenol, 1-methyl-2-hydroxy-4-aminobenzene, 3-N,N-dimethyl aminophenol, 2.6-dihydroxy-3.5-dimethoxypyridine, 5-amino-3-methylphenol, 6-amino-3-methylphenol, 3-amino-2-methylamino-6-methoxypyridine, 2-amino-3-hydroxy-pyridine, 2-dimethylamino-5-aminopyridine, 2,6-diaminopyridine, 1,3-diaminobenzene, 1-amino-3-(2'-hy-droxyethylamino)benzene, 1-amino-3-[bis(2'-hydroxyethyl)amino]benzene, α-naphthol, 4,6-dichlororesorcinol, 1,3-diamino-toluene, 1-hydroxy naphthalene, 4-hydroxy-1,2-methylenedioxy benzene, 1,5-dihydroxy naphthalene, 1,6-dihydroxy naphthalene, 1,7-dihydroxy naphthalene, 2,7-dihydroxy naphthalene, 1-hydroxy-2-methyl naphthalene, 4-hydroxy-1.2-methyldioxy benzene, 2,4-diamino-3-chlorophenol, 5-amino-2-methoxyphenol and/or 1-methoxy-2-amino-4-(2'-hydroxyethyl amino)benzene or the water-soluble salts thereof. However, this shall not exclude the addition of further developing and coupling substances.

The weight proportion of the named developing substances to the additional developing and coupling substances ranges between about 1:8 to 8:1, preferably about 1:5 to 5:1, in particular 1:2 to 2:1. In the hair dyeing compositions according to the invention, the coupling substance(s) as reaction partners of the developing substance(s) are present in approximately the same molecular proportions as the developing substances, i.e. in amounts from 0.01% to 5.0%, preferably 0.05% to 4%, in particular 0.1% to 3% by weight, calculated to the total composition (excluding the oxidizing agent), whereby these figures are always related to the proportion of free base.

The composition of the present invention can comprise additionally direct dyes of neutral, cationic and anionic character. Some examples to suitable cationic dyes are Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Red 2, Basic Red 12 Basic Red 22, Basic Red 51, Basic Red 76, Basic Violet 1, Basic Violet 2, Basic Violet 3, Basic Violet 10, Basic Violet 14 and Basic Yellow 57. According to the invention, suitable cationic dyestuffs are in principal those any available on the market for cosmetic hair colouring applications. For this purpose, special reference is made to the PCT application WO 95/15144 of Ciba-Geigy AG. The content of the PCT application WO 95/15144 is by reference incorporated here.

Examples to suitable direct acting anionic dyes are Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No.10, D&C Orange No.11, D&C Red No. 21, D&C Red No. 27, D&C Red No. 33, D&C Violet 2, D&C Yellow No. 7, D&C Yellow No. 8, D&C Yellow No.10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium.

Some examples to those suitable neutral dyes (HC dyes), so called nitro dyes, are HC Blue No.2, HC Blue No.4, HC Blue No.5, HC Blue No.6, HC Blue No.7, HC Blue No.8, HC Blue No.9, HC Blue No.10, HC Blue No.11, HC Blue No.12, HC Blue No.13, HC Brown No.1, HC Brown No.2, HC Green No.1, HC Orange No.1, HC Orange No.2, HC Orange No.3, HC Orange No.5, HC Red BN, HC Red No.1, HC Red No.3, HC Red No.7, HC Red No.8, HC Red No.9, HC Red No.10, HC Red No.11, HC Red No.13, HC Red No.54, HC Red No.14, HC Violet BS, HC Violet No.1, HC Violet No.2, HC Yellow No.2, HC Yellow No.4, HC Yellow No.5, HC Yellow No.6, HC Yellow No.7, HC Yellow No.8, HC Yellow No.9, HC Yellow No.10, HC Yellow No.1 1, HC Yellow No.12, HC Yellow No.13, HC Yellow No.14, HC Yellow No.15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

Plant dyestuffs can also be used alone or in combination with synthetic direct-acting dyestuffs, for example henna (red or black), alkanna root, laccaic acid, indigo, logwood powder, madder root and rhubarb powder, etc.

According to the invention, coloring composition comprises direct hair dyes at a total concentration of 0.01 to 5%, preferably 0.05 to 3%, more preferably 0.1 to 2% by weight calculated to total composition excluding the oxidative composition.

It is further embodiment of the present inventions that colouring compositions comprise oxidative dyestuff precursors, and direct acting cationic and anionic dyes as a mixture. In this case the ratio of acidic dyes to cationic dyes by weight is in the range of 3:1 to 1:10, preferably 2:1 to 1:7 and furthermore preferably 2:1 to 1:5.

Hair dyeing composition of the present invention preferably comprise an organopolysiloxane wherein at least one silicium atom is linked to an alkylene group having a heteroatom, in particular a nitrogen atom, with a poly-(N-acyl alkyleneimine) units of the formula

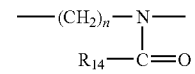

wherein n is a number from 1 to 5 and $R_{14}$ is hydrogen, a $C_1$-$C_{12}$-alkyl or cycloalkyl, aralkyl or aryl group.

Preferred organopolysiloxane polymers are those of the type disclosed in EP-A 640 643, in particular optionally quaternized aminoalkyl, in particular aminopropyl dimethyl polysiloxane/polyethyl oxazoline copolymers of the formula

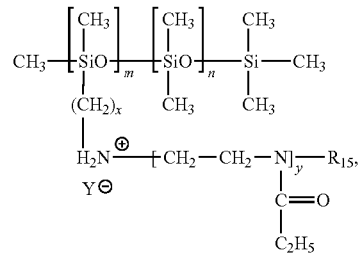

wherein m and n each are numbers from 20 to 10,000, in particular 50 to 7,000, especially 100 to 5,000, x is a number between 1 and 5, preferably 3, and y is a number from 5 to 30, $R_{15}$ is a $C_1$-$C_{12}$-alkyl or aryl group, in particular a methyl, ethyl or benzyl group, and Y- is an anion.

Especially suited are the organopolysiloxanes disclosed under the terms A-1, A-2 and A-3 on pages 12 to 13 of EP-A 640 643. The proportion of graft copolymers in the hair colouring compositions according to the invention ranges from 0.05% to 5%, preferably 0.1% to 2.5%, in particular 0.5% to 1.5% by weight, calculated to the total composition.

Another preferred compound in the colouring composition is of ceramide type of compounds according to general formula

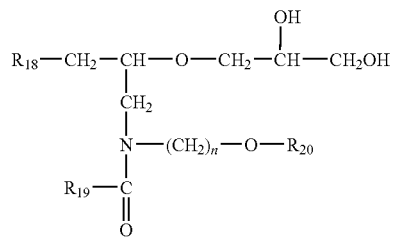

where $R_{18}$ and $R_{19}$ are independent from each other alkyl or alkenyl group mit 10 to 22 carbon atoms, $R_{20}$ is methyl, ethyl, n-propyl or isopropyl group and n is a number between 1 to 6, preferably 2 or 3. The concentration of ceramide type of compound in colouring compositions of the present invention can be in the range of 0.01 to 2 and especially 0.01 to 1% by weight calculated to the total composition.

The compositions of the present invention preferably comprise one or more ubiquinone of the formula.

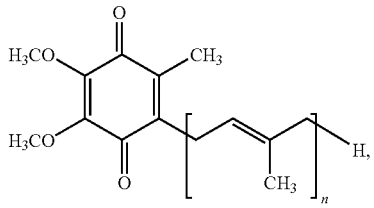

wherein n is a number from 1 to 10. Concentration of ubichinones in the compositions of the present invention can vary between 0.001% and 10% by weight, calculated to the total composition excluding oxidizing agent.

Coloring composition of the present invention can certainly comprise compounds for accelerating (catalysts) the oxidative dyeing keratin fibres such as iodine salts i.e. potassium or sodium iodide and/or dihydroxy acetone.

The hair dyeing compositions according to the invention can comprise the basic substances and additives customarily found in such compositions, conditioning agents, etc., known as state of the art and described, for example, in the monography of K. Schrader, "Grundlagen und Rezepturen der Kosmetika", 2nd Ed. (Hüthig Buch Verlag, Heidelberg, 1989), pp. 782 to 815. They can be prepared as solutions, creams, gels or also in the form of aerosol products; suitable carrier material compositions are known as state of the art.

For application, the oxidation dyestuff precursor is mixed with an oxidizing agent. The preferred oxidizing agent is hydrogen peroxide, for example in a concentration of 2 to 12% by weight. However, the use of other peroxides such as urea peroxide and melamine peroxide is also possible. The oxidizing base can comprise surfactants of anioni, nonionic and zwitterionic character wherein anionic and nonionic surfactants are preferred and anionic and/or nonionic polymers for thickening purposes. It is certainly possible to use anionic polymers especially those of acrylate types for thickening purposes wherein thickening is achieved after mixing with alkaline oxidative dyes comprising composition at neutral to alkaline pH. pH of the oxidizing composition is in principal acidic below pH 5.0.

Accordingly, further object of the present invention is a hair colouring process wherein a composition comprising at least one oxidative dyestuff precursor and yogurt powder is mixed with an oxidizing composition comprising an oxidizing agent and applied onto hair and left on the hair for 10 to 45 min at a temperature of 20 to 40° C. and subsequently rinsed off with water.

Still further object of the present invention is a kit for colouring hair comprising two composition A and B wherein composition A comprises at least one oxidative dyesuff precursor and yogurt powder and the composition B comprises at least one oxidizing agent.

As an alternative to peroxide oxidation, it is also possible to achieve the oxidation by air, for example, by applying onto the hair a composition comprising an oxidation dyestuff precursor as aerosol foam and leaving to process for about 15 to 20 minutes.

The pH-value of the ready-to-use hair dyeing composition, i.e. after mixing with peroxide, can be between 5 and 12, preferably 6-11, more preferably 6.8 to 10.

The following examples are to illustrate the invention without limiting it.

| Carrier | |
|---|---|
| Stearyl alcohol | 8.0 (% by wt.) |
| Coco fatty acid monoethanolamide | 4.5 |
| 1.2-Propanediol mono/distearate | 1.3 |
| Coco fatty alcohol polyglycolether | 4.0 |
| Sodium lauryl sulfate | 1.0 |
| Oleic acid | 2.0 |
| 1.2-Propanediol | 1.5 |
| Na-EDTA | 0.5 |
| Yogurt powder | 0.7 |
| Sodium sulfite | 1.0 |
| Protein hydrolyzate | 0.5 |
| Ceramide according to formula where $R_{18}$ and $R_{19}$ are C16 and $R_{20}$ is ethyl | 0.2 |
| Ascorbic acid | 0.2 |
| Organopolisiloxane according to EP640643 | 0.3 |
| Compound A-1 | |
| Perfume | 0.4 |
| Ubichinone 10 | 0.1 |
| Ammonia, 25% | 1.0 |
| Ammonium chloride | 0.5 |
| Panthenol | 0.8 |
| Water | ad 100.00 |

The dyestuff combinations either oxidative or direct dyes were incorporated into this carrier, whereby the water content was reduced accordingly.

EXAMPLE 1

Hair colouring composition comprising following oxidative dyes was prepared using the above given carrier composition.

| | |
|---|---|
| 2,5,6-Triamino-4-hydroxypyrimidinsulfat | 0.01 |
| 2,5-Diaminotoluolsulfat | 0.55 |
| 4-Chlorresorcin | 0.17 |
| Resorcin | 0.05 |
| 3-Aminophenol | 0.03 |

For comparative purposes the above mentioned colouring composition was prepared in which yogurt powder was excluded form the composition.

In a half side test both compositions were tested with 10 female volunteers. The above composition was mixed with hydrogen peroxide lotion comprising 6% hydrogen peroxide at a weight ratio of 1:1 prior to application onto hair. The pH was 9.8. Three hair dressers were asked to evaluate first of all the color and hair combability. The color was found to be equal, no differences were observed at all. In combability major differences were observed. In 5 case the combability was judged to be much better, in 3 cases combability was found to be better and in remaining 2 case it was found to be slightly better for the side coloured with colouring composition comprising yogurt powder. These test results show clearly that incorporation of yogurt powder into oxidative colouring composition improves hair combability after colouring.

Similar results were obtained with the following examples.

EXAMPLE 2

| | |
|---|---|
| 2,5,6-Triamino-4-hydroxypyrimidinsulfat | 1.05 |
| 4-Amino hydroxy toluol | 0.54 |
| Basic red 51 | 0.10 |
| Acid red 52 | 0.05 |

The composition was mixed with 6% hydrogen peroxide lotion prior to application and the mixed composition had a pH of 9.8.

EXAMPLE 3

| | |
|---|---|
| 2,5,6-Triamino-4-hydroxypyrimidinsulfat | 0.02 |
| 2,5-Diaminotoluolsulfat | 0.43 |
| HC Yellow No 5 | 0.02 |
| 4-Amino hydroxy toluol | 0.02 |
| Resorcin | 0.10 |
| 3-Aminophenol | 0.07 |

The composition was mixed with 2% hydrogen peroxide lotion prior to application and the mixed composition had a pH of 6.8.

EXAMPLE 4

| | |
|---|---|
| 1-Hydroxyethyl-4,5-diaminopyrazole sulfate | 1.05 |
| 4-amino-3-hydroxytoluene | 0.54 |
| Basic red 51 | 0.10 |
| Acid red 52 | 0.05 |

The composition was mixed with 6% hydrogen peroxide lotion prior to application and the mixed composition had a pH of 9.8.

The invention claimed is:

1. Process for coloring hair comprising mixing a composition comprising at least one oxidative dyestuff precursor and yogurt powder with an oxidizing composition comprising an oxidizing agent to form a mixture, applying the mixture onto hair, leaving the mixture on the hair for 10 to 45 minutes at a temperature of 20 to 40° C., and subsequently rinsing off with water.

2. The process according to claim 1, wherein the composition further comprises at least one coupling agent.

3. The process according to claim 1, wherein the composition further comprises at least one direct dye.

4. The process according to claim 1, wherein the yogurt powder is at a concentration of 0.01 to 5% by weight calculated to total composition excluding oxidizing composition.

5. The process according to claim 1, wherein the composition further comprises organosiloxane polymer according to formula

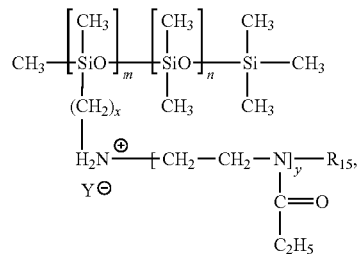

wherein m and n each are numbers from 20 to 10,000, x is a number between 1 and 5, and y is a number from 5 to 30, $R_{15}$ is a C1-C12-alkyl or aryl group.

6. The process according to claim 1, wherein the composition further comprises at least one ceramide type compound according to the formula

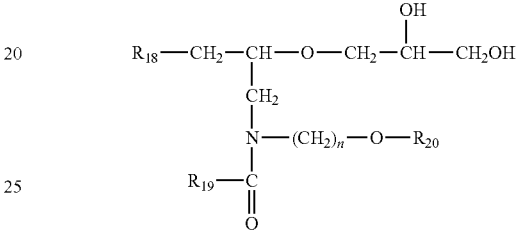

where $R_{18}$ and $R_{19}$ are independent from each other alkyl- or alkenyl group with 10 to 22 carbon atoms, $R_{20}$ is methyl, ethyl, n-propyl or isopropyl group and n is a number between 1 to 6, 2 or 3.

7. The process according to claim 1, wherein the composition further comprises at least one ubiquinone of the formula

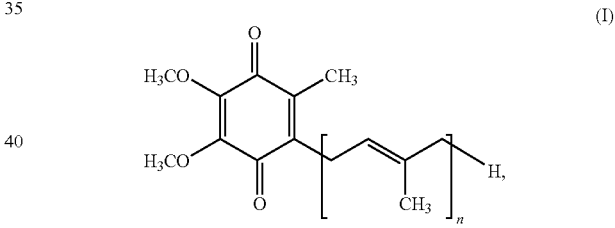

(I)

wherein n is a number from 1 to 10.

8. The process according to claim 1, wherein the composition further comprises potassium or sodium iodide and/or dihydroxyacetone for as catalysts.

9. The process according to claim 1, wherein the composition has pH between 5 and 12 after mixing with the oxidizing composition.

10. The process according to claim 5, wherein the alkyl group is selected from the group consisting of methyl and ethyl and the aryl group represented by a benzyl group, and $Y^-$ is an anion.

11. The process according to claim 9, wherein the oxidizing composition is a hydrogen peroxide solution.

12. The process for coloring hair according to claim 1, wherein oxidizing agent is hydrogen peroxide.

13. Hair coloring kit comprising two compositions A and B which are mixed prior to application onto hair wherein composition A is the composition comprising at least one oxidative dyestuff precursor and yogurt powder and the composition B comprises at least one oxidizing agent.

14. The hair coloring kit according to claim 13, wherein the oxidizing agent is hydrogen peroxide.

* * * * *